(12) United States Patent
Shan

(10) Patent No.: US 10,543,055 B2
(45) Date of Patent: Jan. 28, 2020

(54) STRUCTURE FOR AUTOMATICALLY IDENTIFYING PREDETERMINED LENGTH OF TOURNIQUETS AND METHOD FOR IDENTIFYING PREDETERMINED LENGTH

(71) Applicant: Xijie Shan, Wuxi (CN)

(72) Inventor: Xijie Shan, Wuxi (CN)

(73) Assignee: WUXI KAISHUN MEDICAL DEVICE MANUFACTURING CO., LTD., Wuxi, Jiangsu (CN)

( * ) Notice: Subject to any disclaimer, the term of this patent is extended or adjusted under 35 U.S.C. 154(b) by 585 days.

(21) Appl. No.: 15/557,259

(22) PCT Filed: Jan. 21, 2015

(86) PCT No.: PCT/CN2015/071236
§ 371 (c)(1),
(2) Date: Dec. 21, 2017

(87) PCT Pub. No.: WO2015/110017
PCT Pub. Date: Jul. 30, 2015

(65) Prior Publication Data
US 2018/0116752 A1    May 3, 2018

(30) Foreign Application Priority Data

Jan. 22, 2014  (CN) .......................... 2014 1 0030186
Apr. 9, 2014   (CN) .......................... 2014 1 0141425

(51) Int. Cl.
*G01B 5/00*     (2006.01)
*A61B 90/00*    (2016.01)
(Continued)

(52) U.S. Cl.
CPC .......... *A61B 90/08* (2016.02); *A61B 17/1322* (2013.01); *A61B 50/30* (2016.02);
(Continued)

(58) Field of Classification Search
CPC ........................... A61B 50/30; A61B 17/1322
(Continued)

(56) References Cited

U.S. PATENT DOCUMENTS 840,047 A  *  1/1907  Davis ..................... B65H 75/18
                                                    33/733
1,563,100 A  *  11/1925  Myers ..................... G01B 3/02
                                                    33/733
(Continued)

FOREIGN PATENT DOCUMENTS

CN        201353176         12/2009
CN        202191330         4/2012
(Continued)

OTHER PUBLICATIONS

International Search Report for PCT/CN2015/071236, dated Mar. 27, 2015, 6 pages.

*Primary Examiner* — George B Bennett
(74) *Attorney, Agent, or Firm* — Nixon & Vanderhye P.C.

(57) ABSTRACT

Disclosed are a structure for automatically identifying a predetermined length of a tourniquet, and a method for quickly identifying the predetermined length. The structure for automatically identifying a predetermined length of a tourniquet comprises a box and tourniquets, wherein the box has at least one receiving cavity in which the tourniquets are placed and an opening configured to be passed through by an end of the tourniquets, wherein apertures are formed in the tourniquets at an interval of the predetermined length in a longitudinal direction of the tourniquets, the box is provided with a protrusion configured to cooperate with the apertures during the extraction of the tourniquets, and the apertures are configured to identify the predetermined length of the tourniquets and facilitate tearing off of the tourniquets during the tearing off of the tourniquets.

8 Claims, 10 Drawing Sheets

(51) Int. Cl.
  *A61B 17/132*  (2006.01)
  *A61B 50/30*  (2016.01)
(52) U.S. Cl.
  CPC ... *A61B 2090/037* (2016.02); *A61B 2090/061* (2016.02); *A61B 2090/0807* (2016.02)
(58) Field of Classification Search
  USPC .......................................................... 33/733
  See application file for complete search history.

(56) References Cited

U.S. PATENT DOCUMENTS

| | | |
|---|---|---|
| 2,288,801 A | 7/1942 | Goldsmith |
| 2018/0228565 A1* | 8/2018 | Takken ..................... A61L 2/26 |

FOREIGN PATENT DOCUMENTS

| | | |
|---|---|---|
| CN | 203411144 | 1/2014 |
| CN | 203815528 | 9/2014 |
| CN | 203815601 | 9/2014 |
| CN | 203828997 | 9/2014 |
| WO | WO 2006/097739 | 9/2006 |

* cited by examiner

STRUCTURE FOR AUTOMATICALLY IDENTIFYING PREDETERMINED LENGTH OF TOURNIQUETS AND METHOD FOR IDENTIFYING PREDETERMINED LENGTH

TECHNICAL FIELD

The present application relates to medical instruments, and particularly to a structure including tourniquets and a matching box, as well as a method for quickly tearing off a tourniquet of a predetermined length from the box and for automatically identifying the predetermined length during extracting the tourniquet.

TECHNICAL BACKGROUND

The existing rubber tourniquet is defective for repeated usage, cross-usage, and insufficient disinfection, and thus is unsanitary in use.

As an improved alternative to the rubber tourniquet, disposal tourniquets mostly have an elongated sheet shape and packaged individually, as a result, nursing staff suffers from a low work efficiency because of the need for frequently unpackaging the tourniquets for using the same.

In the case of continuously-extractable tourniquets, in order to separate an individual tourniquet from the continuous tourniquets, a user has to focus on the extracted length of the tourniquet in extraction, because the box matching with the continuous tourniquets cannot automatically identify the tearing position at the predetermined length of the tourniquet. In the prior art, a method based on supplementary identifier is generally adopted. For example, in Chinese patent No. 200920265929.1, a remarkable identifier such as a dot in red or other color is placed adjacent to the tearing line to reminder the user about the position of the tearing line of the tourniquet, so that the user can subsequently clamp the tourniquet adjacent to the tearing line by other supplementary mechanism such as clamping bars or teethed bars, and tears and disconnects the individual tourniquet at the predetermined position.

However, the user still needs to stare at the tourniquet and observe the extracted length of the tourniquet during the entire extraction, and stops extraction when seeing the identifier remaindering of the tearing line. Then, the tourniquet is clamped by the supplementary mechanism and torn so that an individual tourniquet is separated from the continuous tourniquets. The user is required to stare at the tourniquet during the above-mentioned whole process, and both hands are used for the clamping and tearing, thereby increasing the work load of the nursing staff and causing inconvenience in use.

Therefore, there is a need in the industry for free of eyes and hands of the user during the extraction of the tourniquet, and simplifying the operations.

SUMMARY

Accordingly, an object of the present application is to provide a structure capable of quickly disconnecting the tourniquet and automatically identifying the predetermined length of the tourniquet.

The object is achieved as below.

A structure capable of automatically identifying the predetermined length of a tourniquet includes a box and continuous tourniquets, where the box at least includes a receiving cavity into which the continuous tourniquets are placed and an opening through which an end of the tourniquets passes; apertures are arranged in the continuous tourniquets at an interval of a predetermined length along the longitudinal direction of the tourniquets, and the box is provided with at least one protrusion matching with the apertures, so that the apertures cooperate with the at least one protrusion during the extraction of the tourniquets; in tearing off the tourniquet, the apertures are used for positioning and identifying the predetermined length of the tourniquet and facilitating the tearing off of the tourniquet at the apertures. Here, the continuous tourniquets are composed of N individual tourniquets each of a predetermined length. The continuous tourniquets may be folded or rolled within the receiving cavity.

The apertures may be arranged at the same or different intervals along the longitudinal direction of the tourniquets. Alternatively, sets of apertures, each including at least two apertures such as 2 or 3 apertures, are formed in the tourniquets at an interval of a predetermined length along the longitudinal direction of the tourniquets. The set of apertures in each individual tourniquet are arranged in line along the width direction of the tourniquet. At least one aperture is formed in each individual tourniquet.

Further, tearing lines are formed in the tourniquets. The apertures may be located in the tearing lines or at one or both sides of the tearing lines, adjacent to the tearing lines. That is, at least one tearing line is arranged between two adjacent individual tourniquets.

Further, the apertures cooperate with the protrusions, respectively, when the tourniquet is extracted. For example, one of the apertures cooperates with one of the protrusions, or two of the apertures cooperate with two of the protrusions. Alternatively, one of the apertures may cooperate with two or more of the protrusions.

Further, the above-mentioned structure may further include a fixed shaft fixed to the box, and the fixed shaft extends through a seat on which the tourniquets are wounded. The seat is rotatable relative to the fixed shaft and may be a damped bearing.

Further, the above-mentioned structure may further include a fixed shaft, which is fixed to the box and cooperates with a bearing extending through a seat on which the tourniquets are wounded.

Further, a damper is provided between the seat and the box, and is configured to avoid unintentional rotation of the seat caused by rotatory inertia during the extraction of the tourniquets.

The above-mentioned structure may further include a bearing, which extends through a seat on which the tourniquets are wounded and cooperates with the seat. The bearing cooperates with the fixed shaft fixed to the box.

Further, the above structure capable of automatically identifying the predetermined length of the tourniquet may further include a lid, which cooperates with the box and is configured to cover the receiving cavity. The structure may include a clamping mechanism which is disposed at the opening and configured to clamp the tourniquet at the opening. When the individual tourniquet is separated from the continuous tourniquets, that is, when the individual tourniquet is torn off at the apertures, the continuous tourniquets are prevented from bouncing back to the receiving cavity due to the elasticity and the restoring force of the tourniquets.

Further, there is further provided with a base which cooperates with the above-mentioned structure. The above-mentioned structure may be disposed on the base or particularly in a groove formed in the base.

Another object of the present application is to provide a method for automatically identifying the predetermined length of the tourniquet and quickly tearing off the tourniquet.

The object of the present application is also achieved as below.

A method for automatically identifying a predetermined length of tourniquets and quickly tearing off the tourniquets, including: preparing a box having at least one receiving cavity; and placing the tourniquets within the receiving cavity, wherein the box is provided with an opening configured to be passed through by an end of the tourniquets, apertures are formed at an interval of the predetermined length in a longitudinal direction in the tourniquets, the box is provided with protrusions which are configured to automatically cooperate with and engage into the apertures during the extraction of the tourniquets out of the opening, so that the predetermined length of the tourniquets is automatically identified by the protrusions, and meanwhile the tourniquets are subjected to, at the apertures, a pair of forces opposite to each other, i.e. a force in the extraction direction of the tourniquets and a force in a direction opposite to the extraction direction applied by the protrusions, to facilitate the fast tearing off of the tourniquets at the apertures.

Further, tearing lines overlapping with the apertures are formed in the tourniquets at an interval in the longitudinal direction, the protrusions automatically cooperate with and extend through the apertures during the extraction of the tourniquets out of the opening, so that the predetermined length of the tourniquets is automatically identified by the protrusions, and meanwhile the quick tearing off of the tourniquets at the aperture and the tearing lines is facilitated by the protrusions.

Alternatively, the method may include: preparing a box having at least one receiving cavity; and placing the tourniquets within the receiving cavity, wherein the box is provided with an opening configured to be passed through by an end of the tourniquets, apertures and tearing lines are respectively formed at an interval of the predetermined length in a longitudinal direction in the tourniquets, with the apertures being adjacent to the tearing lines, wherein the box is provided with protrusions which are configured to automatically cooperate with and engage into the apertures during the extraction of the tourniquets out of the opening, so that the predetermined length of the tourniquets is automatically identified by the protrusions, and meanwhile the quick tearing off of the tourniquets at the tearing lines is facilitated by the protrusions.

The above method according to the present invention eliminates the needs for operations by both hands and for supplementary mechanism such as a tooth-shaped clamping unit. The tourniquets can be simply extracted, and with the stopping of the tourniquets by the protrusion, the tourniquets are applied by a force in the extraction direction by the user and an opposite force by the protrusion simultaneously, to allow for very convenient and quick separation of the individual tourniquet from the continuous tourniquets.

A still further object of the present application is to provide a method for automatically identifying the predetermined length of the tourniquet.

The object of the present application is also achieved as below.

A method for automatically identifying a predetermined length of tourniquets, comprising: preparing a box having at least one receiving cavity; and placing the tourniquets within the receiving cavity, wherein the box is provided with an opening configured to be passed through by an end of the tourniquets, apertures are formed at an interval of the predetermined length in a longitudinal direction in the tourniquets, the box is provided with protrusions which are configured to automatically engage into the apertures to form cooperation with the apertures during the extraction of the tourniquets out of the opening, so that the predetermined length of the tourniquets is automatically identified by the protrusions.

Figure 1:
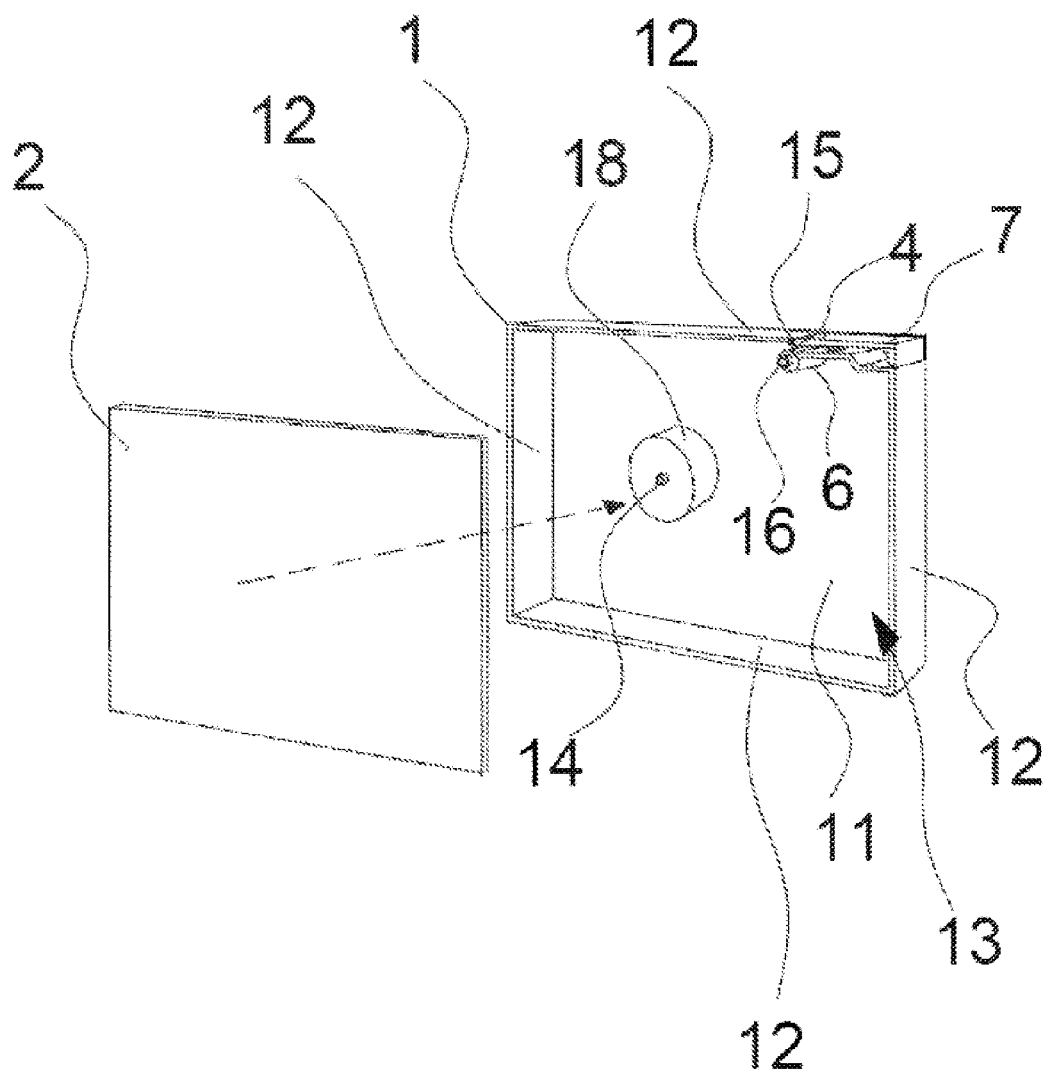
FIG. 1 schematically shows the assembly of a box and a lid according to an embodiment of the invention.
Figure 2:
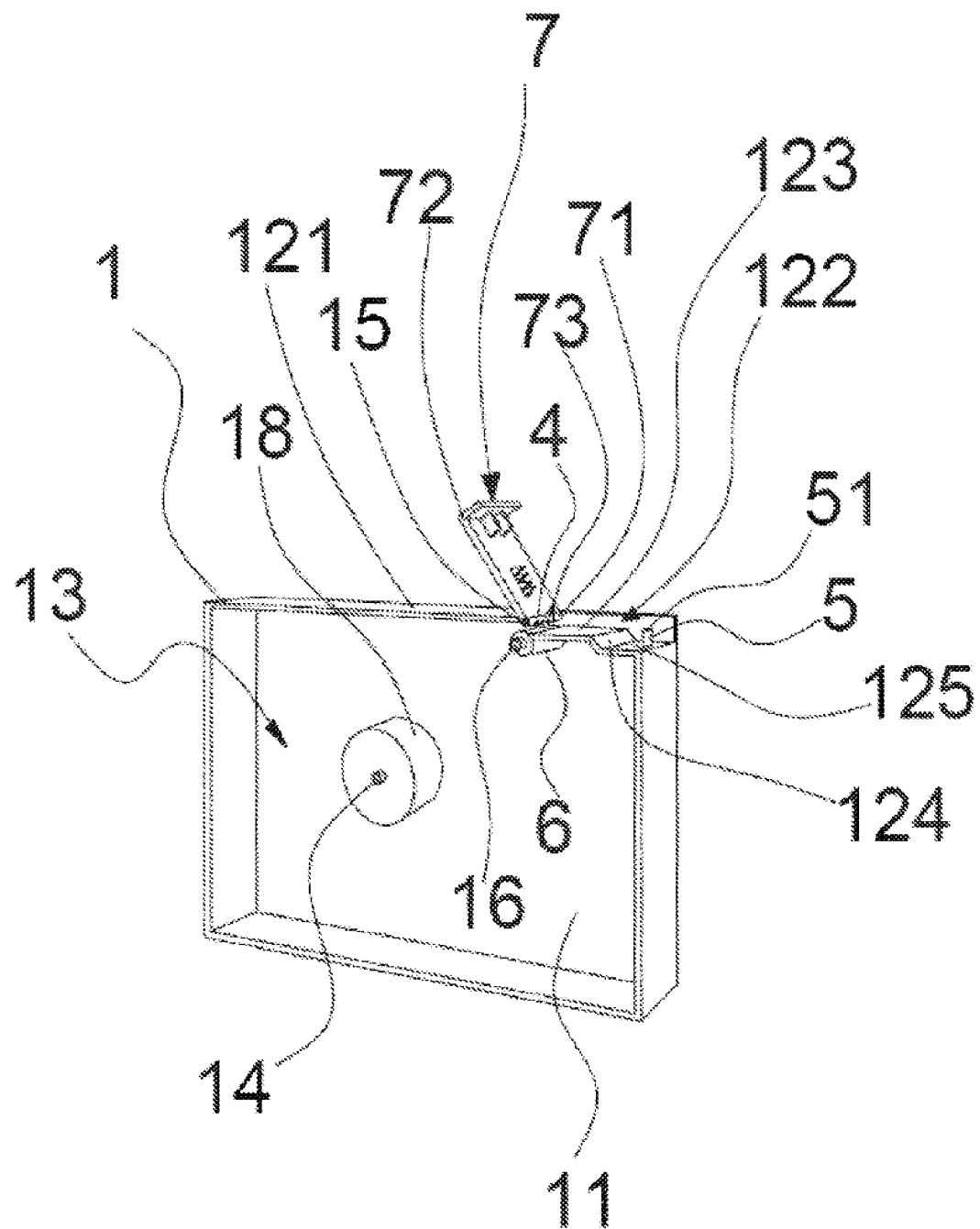
FIG. 2 schematically shows the structure of the box according to an embodiment of the invention.
Figure 3:
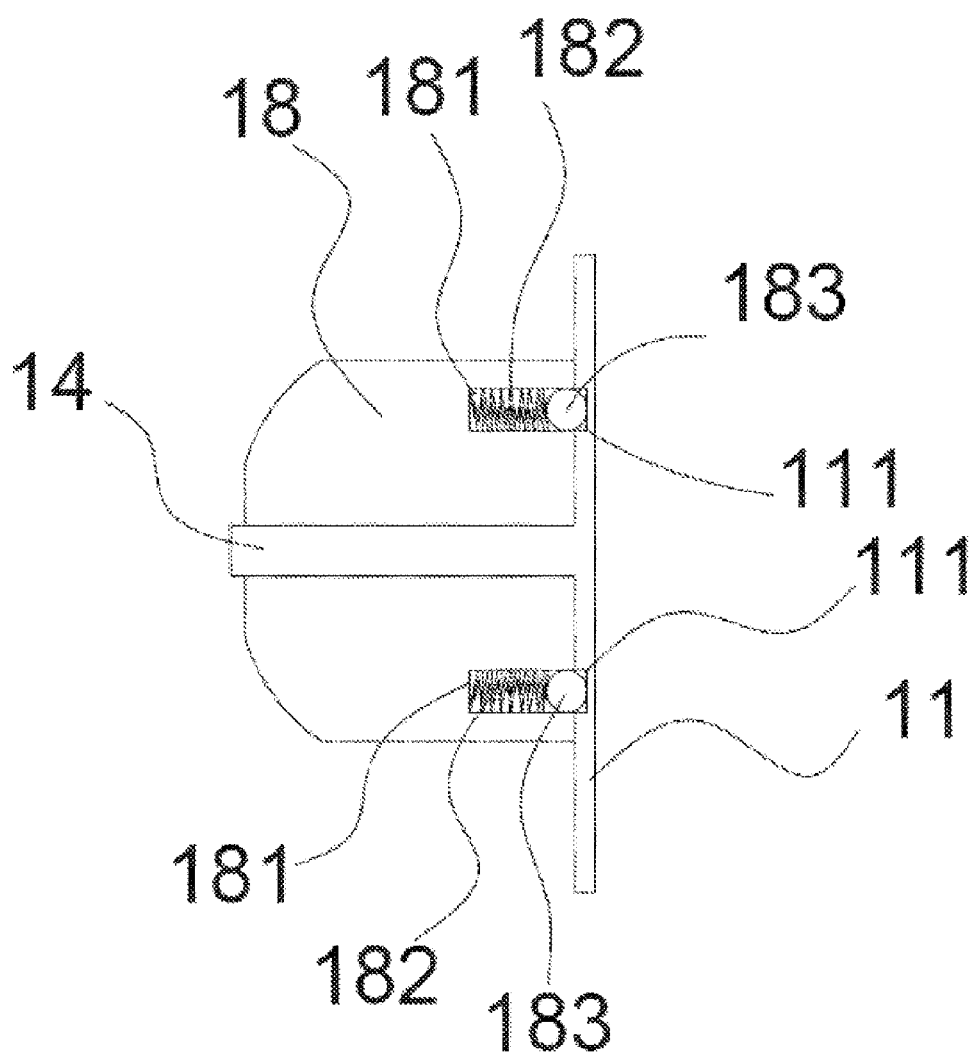
FIG. 3 schematically shows a damper according to an embodiment of the invention.

Reference list 1, 1A: Box,
  11: Bottom side,
    111, 111A, 111B: Groove,
  12: Lateral side,
    121: Lateral side A,   122: Lateral side B,   123: First lateral side,
    124: Second lateral side,   125: Third lateral side,
  13, 13A: Receiving cavity,
  14, 14A, 14B: Fixed shaft,
  15, 15A, 15B: Second shaft,
  16, 16A, 16B: First shaft,
  17: Bearing,   171: Damping bearing,   17A: Bearing,   17B: Bearing,
  18, 18A, 18B: Seat,
    181, 181A, 181B: Blind hole,
  182: Spring,   183: Steel bead,
2: Lid,
3, 3A, 3B: Tourniquets,
  30, 30A, 30B: Individual tourniquet,
  31, 31A, 31B: Aperture,
  32, 32A, 32B: Connecting part,
  38, 38A, 38B: Tearing line,
4, 4A, 4B: Opening,
5, 5A, 5B, 5C, 5D: Protrusion,
  51, 51A, 51B, 51C, 51D: Top point,
6, 6A, 6B: Roller
7, 7A, 7B: Sheet-shaped covering tab, -continued Reference list 71, 71A, 71B: Pivot end,
72, 72A, 72B: Free end,
73: Clamping protrusion.

DETAILED DESCRIPTION OF THE PREFERRED EMBODIMENT

The present disclosure will be further illustrated in detail below in conjunction with FIGS. 1 to 7.

In a first embodiment, the structure for automatically identifying the predetermined length of the tourniquet includes a box 1 and tourniquets 3. The box 1 includes a receiving cavity 13, the tourniquets 3 are wound in roll and placed within the receiving cavity 13, and an opening 4 through which an end of the tourniquets 3 passes is provided on the box 1. Apertures 31 are formed in the tourniquets 3 at an interval of 45 cm in the longitudinal direction of the tourniquets 3. The individual tourniquet may be of a predetermined length of 35 cm, 40 cm and so on, as desired by user needs.

Alternatively, the tourniquets 3 may be folded within the receiving cavity 13.

Protrusions 5 cooperating with the apertures 31 are provided on the box 1, and are configured to cooperate with the apertures 31 during the extraction of the tourniquets 3. The apertures 31 are used in positioning and identifying the predetermined length of the tourniquet 3 and facilitating the fast tearing off of the individual tourniquet 3 at the connecting part 32 around the aperture 31, in order to tear off the tourniquets.

In a second embodiment, the present invention will be further described in combination with FIGS. 1 to 7.

The structure capable of automatically identifying the predetermined length of the tourniquet includes a box 1 and a lid 2. The box 1 has a bottom side 11 and a lateral side 12 connected with the bottom side 11, and a receiving cavity 13 is formed by the lateral side 12 and the bottom side 11. The lid 2 cooperate with the box 1 to close the receiving cavity 13.

A fixed shaft 14 is arranged on the bottom side 11 of the box 1 and may be formed in one piece with the bottom side 11. The fixed shaft 14 protrudes outwards from the bottom side 11 in a normal vector direction of the bottom side 11. The tourniquets 13 are wound on the seat 18 through which the fixed shaft 14 is extended, and the seat 18 is disposed within the receiving cavity 13.

A damper may be arranged between the seat 18 and the box 1. The damper includes a spring 182 and a steel bead 183. The spring 182 and the steel bead 183 are sequentially placed within a blind hole 181 provided in the seat 181, with the steel bead 183 cooperating with a groove 111 formed at the bottom side 11.

An opening 14 configured for extracting the tourniquets is formed at the box 1 so that an end of the tourniquets 3 can pass through the opening 4 to the outside. Here, the continuous tourniquets 3 are constituted by N connected individual tourniquets 30, and an aperture 31 is formed at a connecting part 32 connecting every two adjacent individual tourniquets 30, or alternatively, two or three apertures 31 arranged side by side in the width direction of the tourniquets 30 may be formed at the connecting part 32 connecting the individual tourniquets 30.

Figure 4:
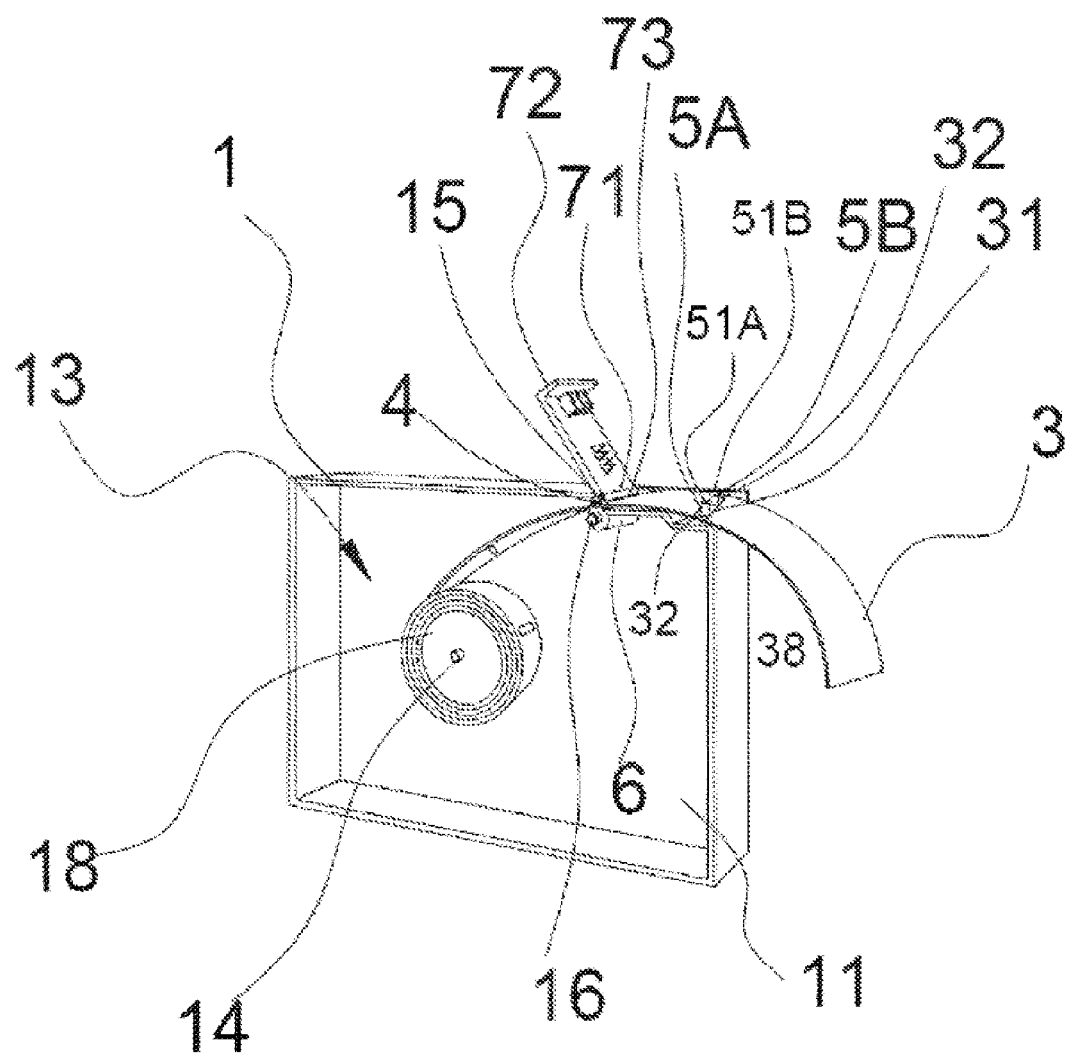
FIG. 4 schematically shows the cooperation of an aperture in the tourniquet with two protrusions on the box according to an embodiment of the invention.

As shown in FIG. 4, protrusions 5A and 5B are formed at a lateral side 12 of the box 1, and the lateral side 12 includes a lateral side A 121 and a lateral side B 122. The lateral side B 122 is constituted by a first lateral side 123, a second lateral side 124 extending from the first lateral side 123 downwards, and a third lateral side 125 extending from the second lateral side 124 horizontally. The first lateral side 123 is lower than the lateral side A 121, and the top point 51A of the protrusion 5A and the top point 51B of the protrusion 5B are higher than the first lateral side 123, so that when the tourniquets 3 are being extracted out, the lower surface of the tourniquets 3 is lower than the top point 51A of the protrusion 5A and the top point 51B of the protrusion 5B.

Here, both of the protrusions 5A and 5B cooperate with one aperture 31, that is, both of the protrusions 5A and 5B can extend through the aperture 31. Alternatively, a plurality of protrusions respectively cooperate with various apertures, or more protrusions cooperate with one aperture. During the extraction of the tourniquets, at least one protrusion cooperates with the aperture in the tourniquet.

In an embodiment, the box 1 is provided with a clamping mechanism which includes a roller 6 and a sheet-shaped covering tab 7. The roller 6 is disposed around the opening 4 via a first shaft 16, and the sheet-shaped covering tab 7 has a pivotal end 71 and a free end 72. The pivotal end 71 is pivotably connected to the box 1 through a second shaft 15 around the opening 4, and is configured to cooperate with the roller 6 to clamp the tourniquets 3 between the pivotal end 71 and the roller 6, so that the tourniquets 3 are tightly pressed at the opening 4, as a result, when an individual tourniquet 30 is separated from the continuous tourniquets 3, the spring-back of the tourniquets 3 towards the receiving cavity 13 due to the elasticity and restoring force of the tourniquets 3 is prevented. The first shaft 16 and the second shaft 15 are fixed to the box 1, and the free end 72 is rotatable about the second shaft 15.

In the process of quickly separating the individual tourniquet from the continuous tourniquets, because the top point 51A of the protrusion 5A and the top point 51B of the protrusion 5B are higher than the first lateral side 123, the lower surface of the tourniquets 3 is lower than the top point 51A of the protrusion 5A and the top point 51B of the protrusion 5B when the tourniquets 3 are being extracted out from the opening 4, therefore, during the extraction of the tourniquets 3, the aperture 31 at the connecting part between two adjacent individual tourniquets 30 automatically cooperates with the protrusions 5A and 5B, that is, the protrusions 5A and 5B automatically extend through and engage with the aperture 31 when the aperture 31 reaches the protrusions 5A and 5B during the extraction, thus the protrusions 5A and 5B automatically identify the predetermined length of the individual tourniquet 30 from the continuous tourniquets 3. At this point, the protrusions 5A and 5B apply a force in a direction opposite to the extraction direction to the tourniquets 3, and hence prevent the further extraction of the tourniquets 3 through the opening 4. With the combination of the force in the extraction direction and the force opposite thereto, the connecting part 32 between the adjacent individual tourniquets is broken, so that the individual tourniquet 30 is quickly separated from the continuous tourniquets 3.

The present invention eliminates the needs for operations by both hands and for supplementary mechanism such as a tooth-shaped clamping unit. The tourniquets can be simply extracted, and with the stopping of the tourniquets by the protrusion 5, the tourniquets are applied by a force in the extraction direction by the user and an opposite force by the protrusion 5 simultaneously, to allow for very convenient and quick separation of the individual tourniquet 30 from the continuous tourniquets 3.

The tourniquets 3 are applied by forces in the horizontal and downwards directions during the extraction, so that the protrusion 5 automatically engages into the aperture 31. Considering that the apertures 31 are disposed at an interval of the predetermined length of the individual tourniquet 30 in the longitudinal direction of the tourniquets 3, one individual tourniquet 30 is identified each time the protrusion 5 engages into the aperture 31.

Figure 5:
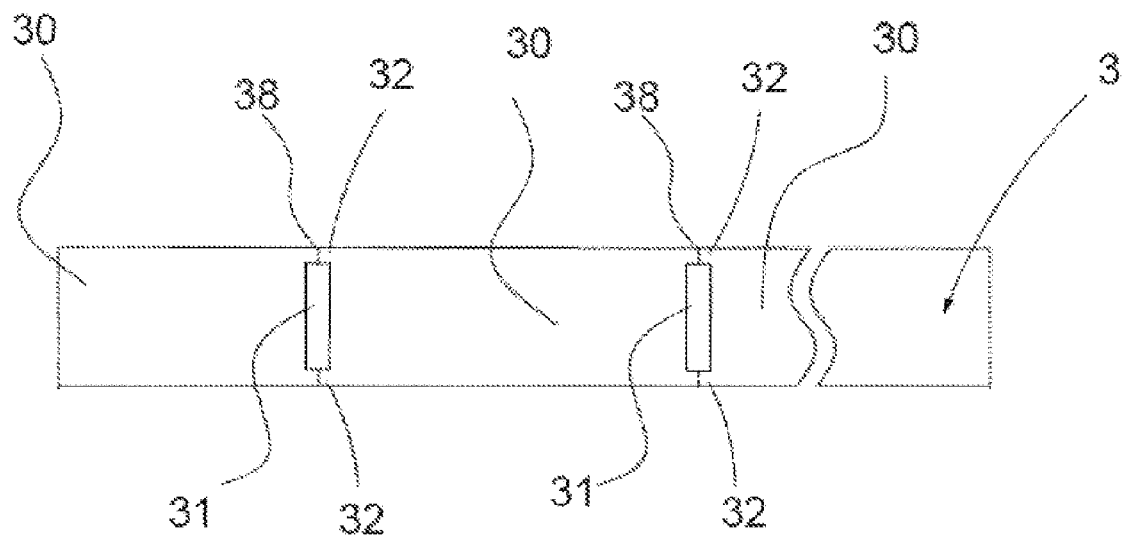
FIG. 5 is a schematic diagram of the tourniquets according to a first embodiment of the invention.
Figure 7:
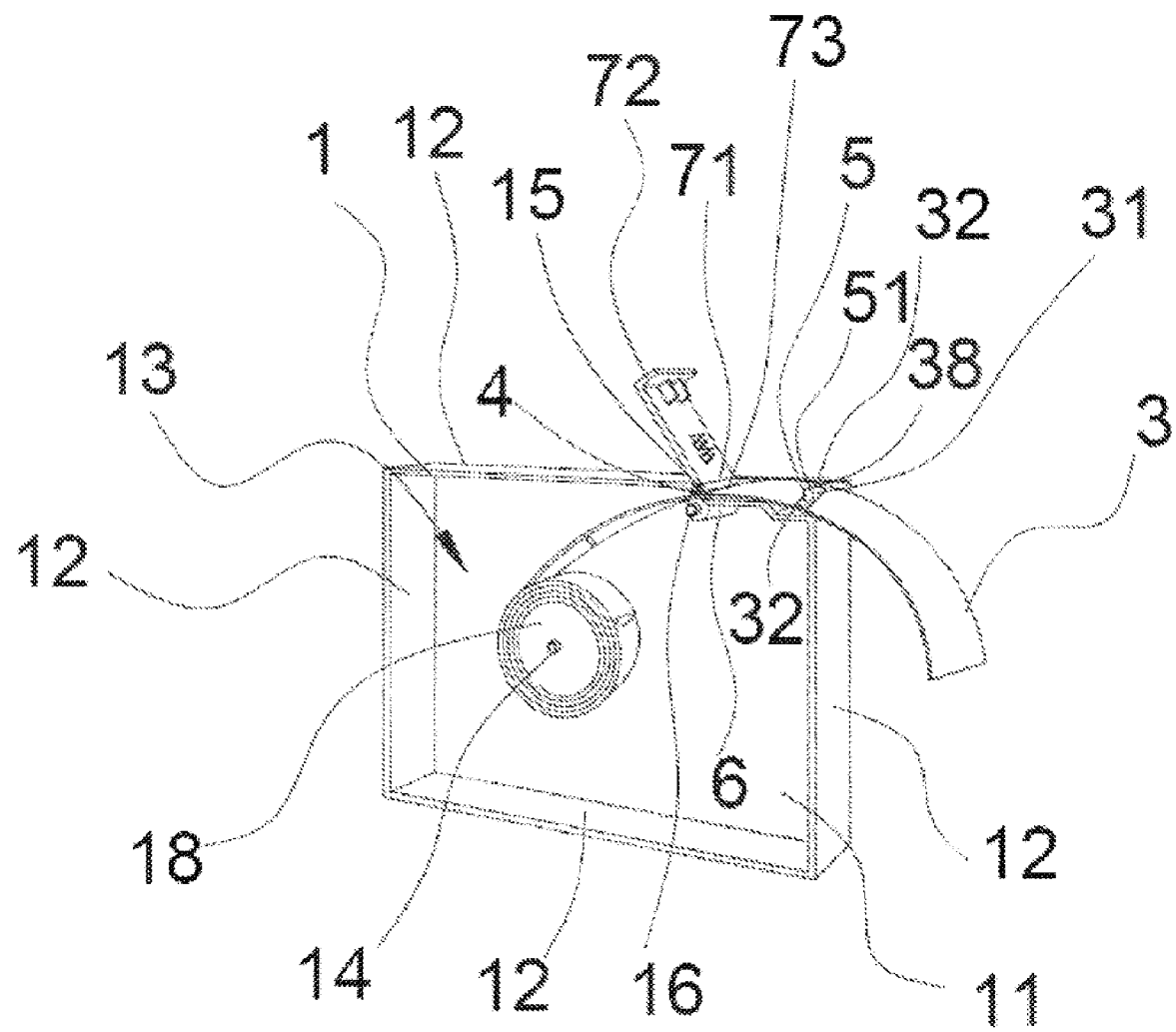
FIG. 7 schematically shows the cooperation of an aperture in the tourniquet with one protrusion on the box according to an embodiment of the invention.
Figure 8:
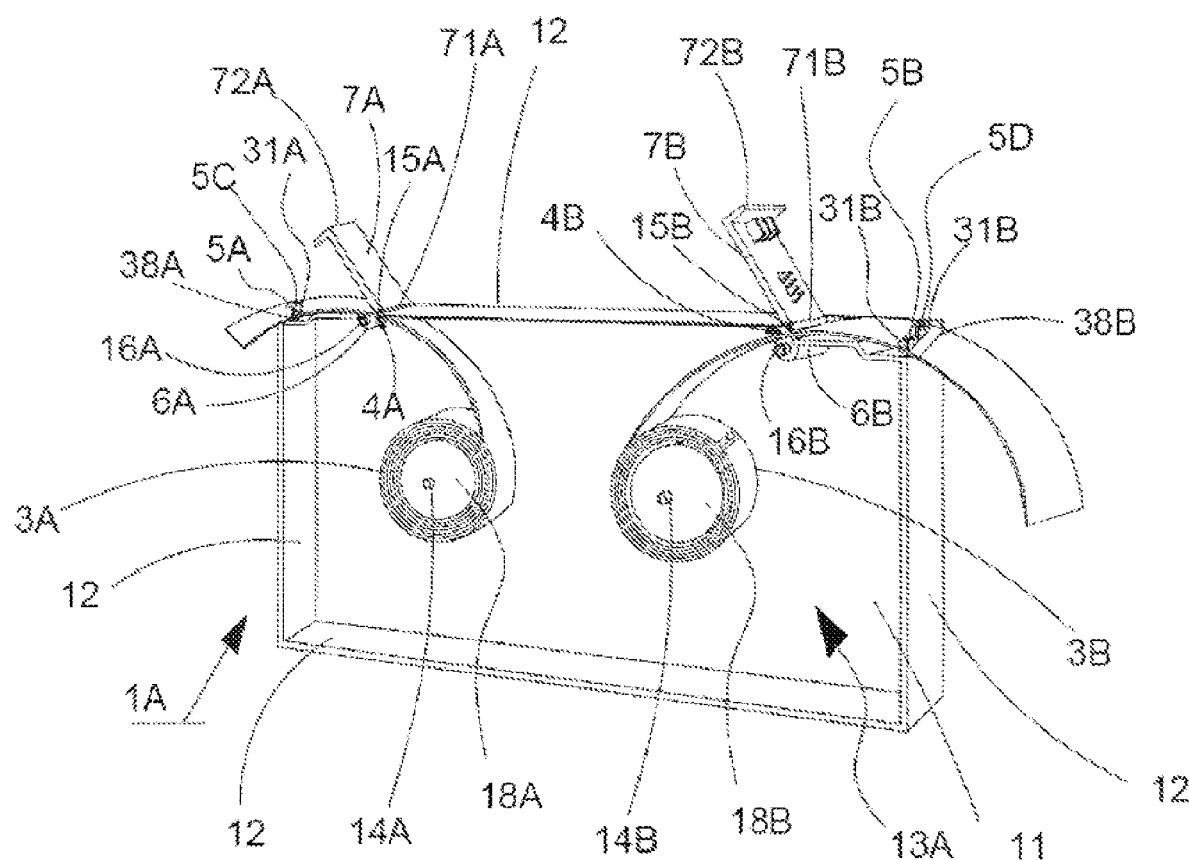
FIG. 8 schematically shows the structure in which two fixed shafts are provided on the bottom side of the box according to an embodiment of the present invention.

In a third embodiment, the present invention will be further described in combination with FIGS. 5 and 7.

The structure capable of automatically identifying the predetermined length of a tourniquet and quickly tearing off the tourniquet includes a box 1 and continuous tourniquets 3. The box 1 has a bottom side 11 and a lateral side 12 connected with the bottom side 11, and a receiving cavity 13 is formed by the lateral side 12 and the bottom side 11 together.

A fixed shaft 14 is arranged on the bottom side 11 of the box 1 and may be formed in one piece with the bottom side 11. The fixed shaft 14 protrudes outwards from the bottom side 11 in a normal vector direction of the bottom side 11. The continuous tourniquets 13 are wound on the seat 18 through which the fixed shaft 14 is extended, and the seat 18 is disposed within the receiving cavity 13.

Figure 6:
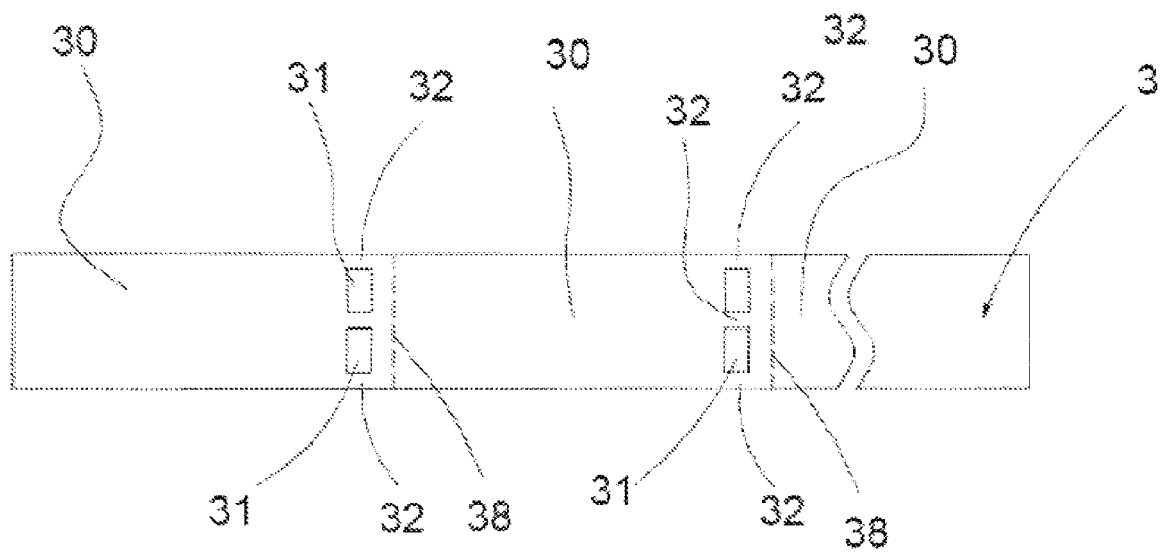
FIG. 6 is a schematic diagram of the tourniquets according to a second embodiment of the invention.

An opening 14 configured for extracting the tourniquets is formed at the box 1 so that an end of the tourniquets 3 can pass through the opening 4 to the outside. Here, the continuous tourniquets 3 are constituted by N connected individual tourniquets 30, and an aperture 31 and a tearing line 38 are formed at a connecting part 32 connecting every two adjacent individual tourniquets 30, with the aperture 31 overlapping the tearing line 38. Alternatively, as shown in FIG. 6, two apertures 31 arranged side by side in the width direction of the tourniquets 30 and the tearing line 38 may be formed at the connecting part 32 connecting the individual tourniquets 30, with the apertures 31 adjacently positioning at a side of the tearing line 38.

The box 1 is provided with a protrusion 5. The lateral side 12 on which the protrusion is formed includes a lateral side A 121 and a lateral side B 122. The lateral side B 122 is constituted by a first lateral side 123, a second lateral side 124 extending from the first lateral side 123 downwards, and a third lateral side 125 extending from the second lateral side 124 horizontally. The first lateral side 123 is lower than the lateral side A 121, and the top point 51 of the protrusion 5 is higher than the first lateral side 123, so that the lower surface of the tourniquets 3 is lower than the top point 51 of the protrusion 5 when the tourniquets 3 engage with the protrusion 5.

During the extraction of the tourniquets 3, the aperture 31 in the tourniquet extracted out of the opening 4 cooperates with the protrusion 5, that is, the protrusion 5 engages into the aperture 31. Alternatively, it is possible that a plurality of protrusions cooperate with various apertures 31, respectively, or a plurality of protrusions cooperate with one aperture 31.

In an embodiment, the box 1 is provided with a clamping mechanism which includes a roller 6 and a sheet-shaped covering tab 7. The roller 6 is disposed around the opening 4 via a first shaft 16, and the sheet-shaped covering tab 7 has a pivotal end 71 and a free end 72. The pivotal end 71 is pivotably connected to the box 1 through a second shaft 15 around the opening 4, and is configured to cooperate with the roller 6 to clamp the tourniquets 3 between the pivotal end 71 and the roller 6, so that the tourniquets 3 are tightly pressed at the opening 4, as a result, when an individual tourniquet 30 is separated from the continuous tourniquets 3, the spring-back of the tourniquets 3 towards the receiving cavity 13 due to the elasticity and restoring force of the tourniquets 3 is prevented. The first shaft 16 and the second shaft 15 are fixed to the box 1, and the free end 72 is rotatable about the second shaft 15.

The protrusion 5 on the box 1 can automatically engage into the aperture 31. Considering that the apertures 31 are disposed at an interval of the predetermined length in the tourniquets 3, the predetermined length is automatically identified when the protrusion 5 engages into the aperture 31 during the extraction of the tourniquets.

Further, when the protrusion 5 engages into the aperture 31 of the tourniquets 3, the connecting part 32 around the aperture 31 of the tourniquets 3 is subjected to a force in the extraction direction and a force in a direction opposite to the extraction direction applied by the protrusion 5, to facilitate the tearing off of the tourniquets 3 at the connecting part 32 and the tearing line 38.

In a fourth embodiment, the present invention will be further described in combination with FIGS. 4, 5 and 6.

A method for automatically identifying the predetermined length of a tourniquet and quickly tearing off the tourniquet includes: preparing a box 1 having a receiving cavity 13; and winding continuous tourniquets 3 onto a seat 18 through which a fixed shaft 14 is extended, and placing the tourniquets 3 within the receiving cavity 13, wherein the box 1 is provided with an opening 4 through which the tourniquets 3 pass, apertures 31 and tearing lines 38 are formed at an interval of the predetermined length in the longitudinal direction in the tourniquets 3, the apertures 31 overlap the tearing lines 38, and the individual tourniquet 30 is of the predetermined length. The box 1 is provided with protrusions 5A and 5B. During extracting an end of the tourniquets 3 out of the opening 4 and subsequently extracting the tourniquets 3, the protrusions 5A and 5B automatically engage into the aperture 31, that is, the protrusions 5 automatically cooperate with the aperture 31, so that the predetermined length of the tourniquets 3 can be automatically identified by engaging the protrusions 5A and 5B into the aperture 31. Meanwhile, when the protrusions 5A and 5B cooperate with the aperture 31, the tourniquets 3 are subjected to a pair of forces opposite to each other, i.e. a force in the extraction direction of the tourniquet and a force in a direction opposite to the extraction direction applied by the protrusions 5A and 5B, to facilitate the fast tearing off of the tourniquets at the connecting part 32 and the tearing line 38.

In a fifth embodiment, the present invention will be further described in combination with FIGS. 4, 5 and 6.

A method for automatically identifying the predetermined length of a tourniquet includes: preparing a box 1 having a receiving cavity 13; and placing the tourniquets 3 within the receiving cavity 13, wherein the box 1 is provided with an opening 4 through which the tourniquets 3 pass, apertures 31 and tearing lines 38 are formed at an interval of the predetermined length in the longitudinal direction in the tourniquets 3, the apertures 31 overlap the tearing lines 38, and an individual tourniquet 30 is of the predetermined length. The box 1 is provided with protrusions 5A and 5B. During extracting the tourniquets 3 out of the opening 4, the protrusions 5A and 5B automatically engage into the aperture 31, that is, the protrusions 5 automatically cooperate with the aperture 31, so that the predetermined length of the tourniquets 3 can be automatically identified by the protrusions 5A and 5B.

In a sixth embodiment, the present invention will be further described in combination with FIGS. 8, 9, 10, 11, 12 and 13.

The structure capable of automatically identifying the predetermined length of a tourniquet and quickly tearing off the tourniquet includes a box 1A, continuous tourniquets 3A and continuous tourniquets 3B.

The box 1A has a bottom side 11 and a lateral side 12 connected with the bottom side 11, and a receiving cavity 13A is formed by the lateral side 12 and the bottom side 11 together. Two fixed shafts 14A and 14B are formed on the same side of the bottom side 11 of the box 1A.

The fixed shafts 14A and 14B may be formed in one piece with the bottom side 11, and both protrude outwards from the bottom side 11 in a normal vector direction of the bottom side 11. In the case where the fixed shafts 14A and 14B are not formed in one piece with the bottom side 11, the fixed shafts 14A and 14B may be alternatively fixed to the bottom side 11 via fixing arrangement.

The seat 18A on which the tourniquets 3A are wounded may cooperate with the fixed shaft 14A. Alternatively, the seat 18A may rotatably attached to the bearing 17A and placed within the receiving cavity 13A.

The seat 18B on which the tourniquets 3B are wounded may cooperate with the fixed shaft 14B. Alternatively, the seat 18B may rotatably attached to the bearing 17B and placed within the receiving cavity 13A.

In the absence of the bearings 17A and 17B, the tourniquets 3A are wounded onto the seat 18A which is rotatably attached to the fixed shaft 14A and placed within the receiving cavity 13A. The seat 18B on which the tourniquets 3B are wounded cooperates with the fixed shaft 14B, and the seat 18B may rotatably attached to the fixed shaft 14B and placed within the receiving cavity 13A.

Alternatively, the seats 18A and 18B are damping bearings, which cooperate with the fixed shafts and on which the tourniquets are wounded.

An opening 4A for extracting the tourniquet 3A and an opening 4B for extracting the tourniquet 3B are arranged on the box 1A.

Apertures 31A are formed in the tourniquets 3A at an interval of the predetermined length in the longitudinal direction of the tourniquets 3A. Alternatively, two apertures 31A arranged side by side in the width direction of the tourniquets are formed at the connecting part 32A connecting the individual tourniquets 30A. Apertures 31B are formed in the tourniquets 3B at an interval of the predetermined length in the longitudinal direction of the tourniquets 3B. Alternatively, two apertures 31B arranged side by side in the width direction of the tourniquets are formed at the connecting part 32B connecting the individual tourniquets 30B. The predetermined direction may be 35 cm, 40 cm, 45 cm, etc.

Figure 11:
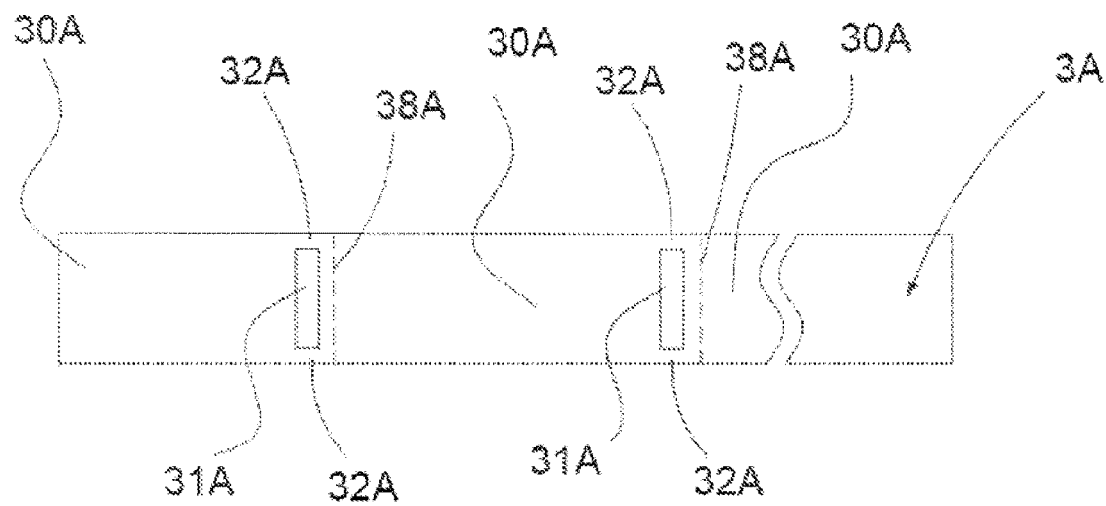
FIG. 11 schematically shows a tourniquet 3A according to an embodiment of the present invention.

As shown in FIG. 11, one end of the tourniquets 3A extends out from the opening 4A. The continuous tourniquets 3A are constituted by N connected individual tourniquets 30A, and an aperture 31A and a tearing line 38A are formed at a connecting part 32A connecting every two adjacent individual tourniquets 30A, with the aperture 31A being positioned at a side of the tearing line 38A.

Figure 12:
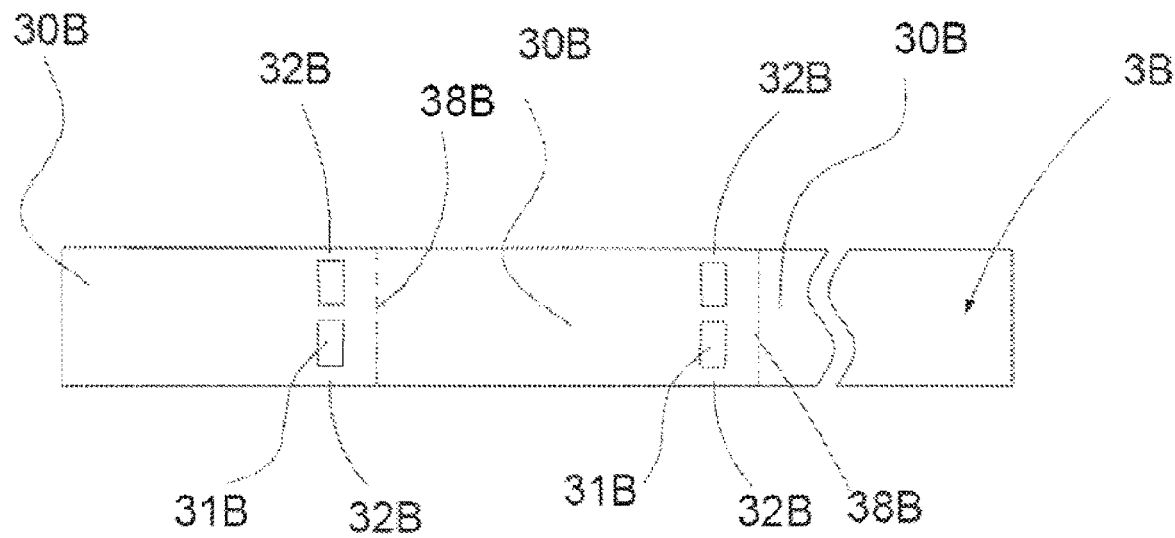
FIG. 12 schematically shows a tourniquet 3B according to an embodiment of the present invention.
Figure 13:
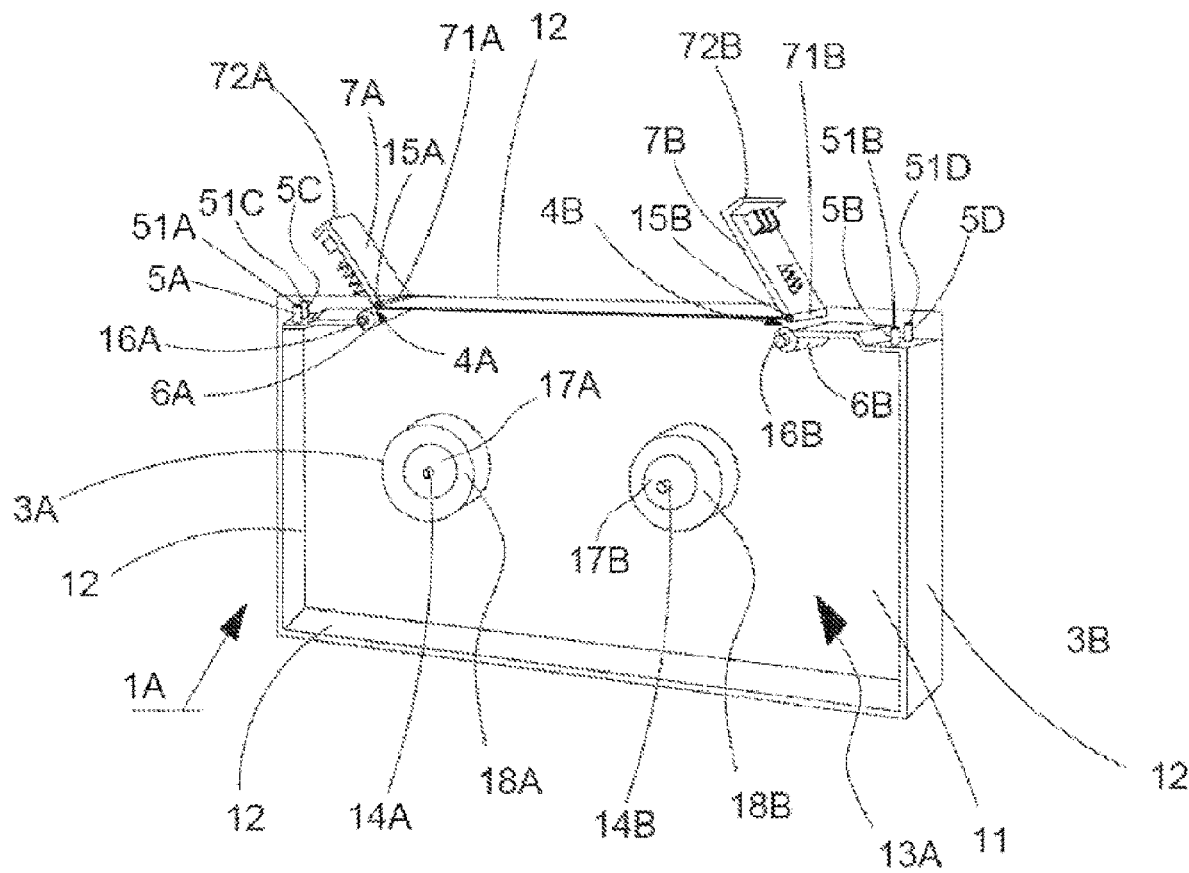
FIG. 13 schematically shows a box having a structure with one receiving cavity and two openings.

As shown in FIG. 12, one end of the tourniquets 3B extends out from the opening 4B. The continuous tourniquets 3B are constituted by N connected individual tourniquets 30B, and an aperture 31B and a tearing line 38B are formed at a connecting part 32B connecting every two adjacent individual tourniquets 30B, with the aperture 31B being positioned at a side of the tearing line 38B.

The box 1A is further provided with protrusions 5A, 5B, 5C and 5D. The protrusions 5A and 5C are disposed at a side of the opening 4A of the box, and the protrusions 5B and 5D are disposed at a side of the opening 4B of the box.

During the extraction of the tourniquets 3A, both of the protrusions 5A and 5C automatically engage into the same aperture 31A because the lower surface of the tourniquets 3A is lower than the top point 51A of the protrusion 5A and the top point 51C of the protrusion 5C. When the tourniquets 3A are continuously extracted after the engagement of the protrusions 5A and 5C into the aperture 31A, the connecting part 32A around the aperture 31A of the tourniquets 3A is subjected to a force in the extraction direction and a force in a direction opposite to the extraction direction applied by the protrusion 5A, and in the absence of the tearing line 38A on the tourniquets 3A, the extraction of the tourniquets leads to the separation of the tourniquets 3A at the connecting part 32A.

If the tourniquets 3A contain the tearing line 38A and the aperture 31A overlaps with the tearing line 38A, the tourniquets 3A are separated at the connecting part 32A and the tearing line 38A during the extraction.

If the tourniquets 3A contain the tearing line 38A and the aperture 31A is arranged at the left side of the tearing line 38A, the tourniquets 3A are separated along the tearing line 38A during the extraction.

During the extraction of the tourniquets 3B, the lower surface of the tourniquets 3B is lower than the top point 51B of the protrusion 5B and the top point 51D of the protrusion 5D, so that the protrusions 5B and 5D automatically engage into the two apertures 31B arranged side by side in the width direction of the tourniquets. When the tourniquets 3A are continuously extracted after the engagement of the protrusions 5B and 5D into the two apertures 31B, the connecting part 32B around the apertures 31B of the tourniquets 3B is subjected to a force in the extraction direction and a force in a direction opposite to the extraction direction applied by the protrusions 5B and 5D, to facilitate the separation of the tourniquets 3B at the connecting part 32B.

If the tourniquets 3B contain the tearing line 38B and the apertures 31B overlap with the tearing line 38B, the tourniquets 3B are separated at the connecting part 32B and the tearing line 38B during the extraction.

If the tourniquets 3B contain the tearing line 38B and the apertures 31B are arranged at the left side of the tearing line 38B, the tourniquets 3B are separated along the tearing line 38B during the extraction.

Figure 9:
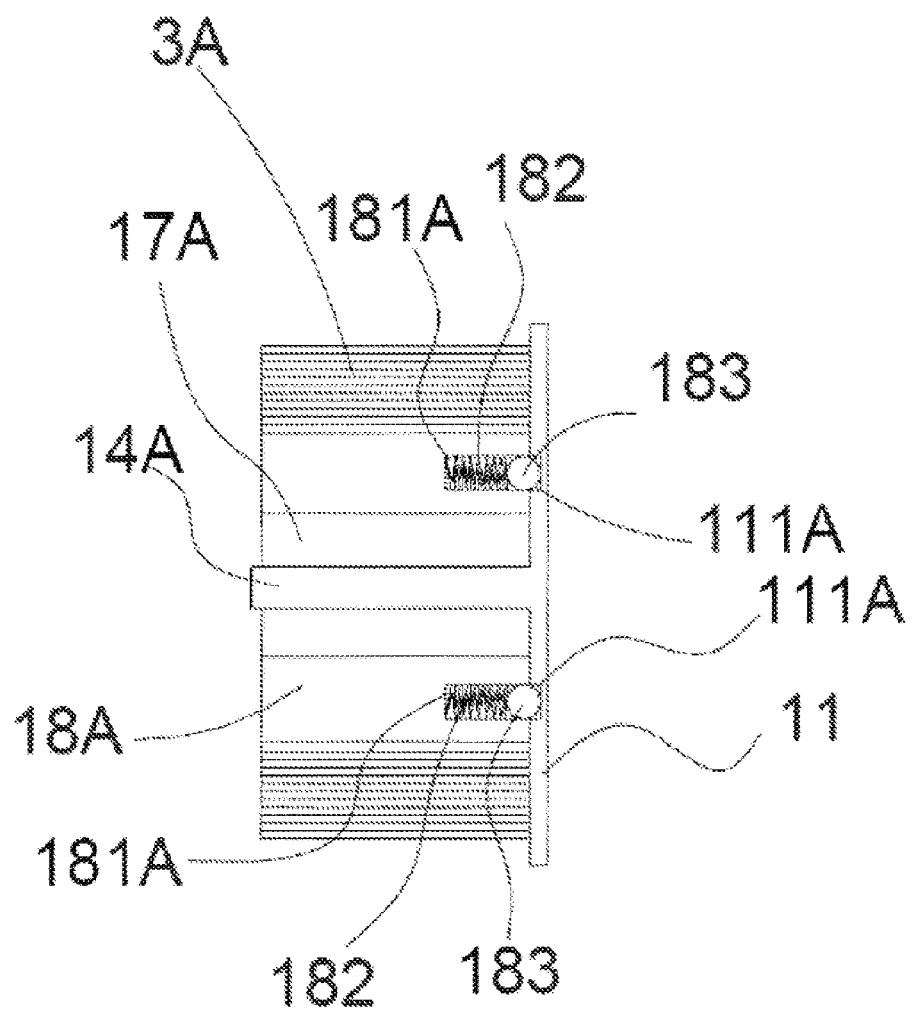
FIG. 9 schematically shows the cooperation between the damper and a groove in the bottom side according to an embodiment of the present invention.

As shown in FIG. 9, if the structure capable of automatically identifying the predetermined length of the tourniquet does not contain a damping bearing, a damping arrangement may be provided between the seat 18A and the bottom side 11. The damping arrangement includes a spring 182 and a steel bead 183, the seat 18A is formed with a blind hole 181A into which the spring 182 and the steel bead 183 are sequentially placed, and the steel bead 183 cooperates with a groove 111 in the bottom side 11.

Figure 10:
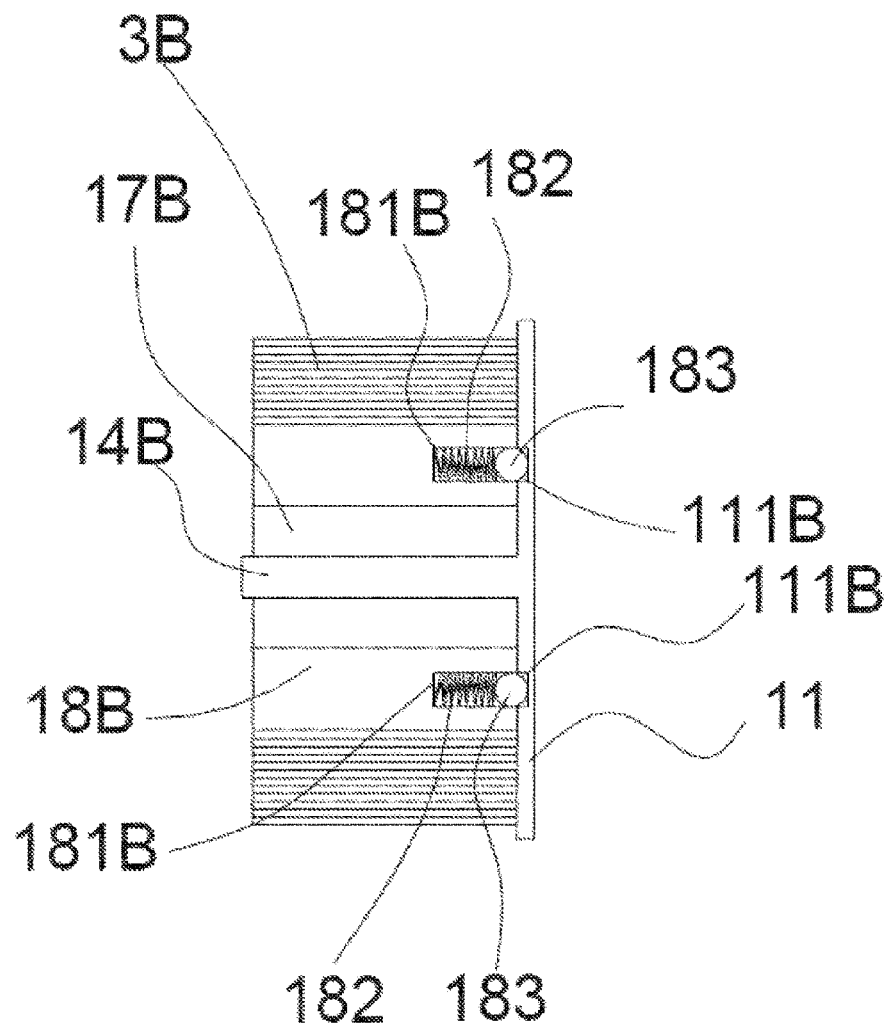
FIG. 10 schematically shows the cooperation between the damper and a groove in the bottom side according to another embodiment of the present invention.

As shown in FIG. 10, if the structure capable of automatically identifying the predetermined length of the tourniquet does not contain a damping bearing, a damping arrangement may be provided between the seat 18B and the bottom side 11. The damping arrangement includes a spring 182 and a steel bead 183, the seat 18B is formed with a blind hole 181B into which the spring 182 and the steel bead 183 are sequentially placed, and the steel bead 183 cooperates with a groove 111B in the bottom side 11.

Here, one protrusion is present at the side of the opening 4A and cooperates with merely one aperture 31A, or a plurality of protrusions are present at the side of the opening 4A and cooperate with various apertures, respectively, or with merely one aperture. During the extraction of the tourniquets, at least one protrusion cooperates with one aperture 31A in the tourniquet, that is, the protrusion engages into the aperture 31A.

It is also possible that one protrusion is present at the side of the opening 4B and cooperates with merely one aperture 31B, or a plurality of protrusions are present at the side of the opening 4B and cooperate with various apertures, respectively, or with merely one aperture. During the extraction of the tourniquets, at least one protrusion cooperates with one aperture 31B in the tourniquet, that is, the protrusion engages into the aperture 31B.

In an embodiment, the box 1A is further provided with a clamping mechanism which includes a roller 6A and a sheet-shaped covering tab 7A, as well as a roller 6B and a sheet-shaped covering tab 7B.

The roller 6A is disposed around the opening 4A via a first shaft 16A, and the sheet-shaped covering tab 7A has a pivotal end 71A and a free end 72A. The pivotal end 71A is pivotably connected to the box 1A through a second shaft 15A around the opening 4A, and is configured to cooperate with the roller 6A to clamp the tourniquets 3A between the pivotal end 71A and the roller 6A, so that the tourniquets 3A are tightly pressed at the opening 4A, as a result, when an individual tourniquet 30A is separated from the continuous tourniquets 3A, the spring-back of the tourniquets 3A towards the receiving cavity 13 due to the elasticity and restoring force of the tourniquets 3A is prevented. The first shaft 16A and the second shaft 15A are fixed to the box 1A, and the free end 72A is rotatable about the second shaft 15A.

The roller 6B is disposed around the opening 4B via a first shaft 16B, and the sheet-shaped covering tab 7B has a pivotal end 71B and a free end 72B. The pivotal end 71B is pivotably connected to the box 1B through a second shaft 15B around the opening 4B, and is configured to cooperate with the roller 6B to clamp the tourniquets 3B between the pivotal end 71B and the roller 6B, so that the tourniquets 3B are tightly pressed at the opening 4B in combination with the clamping protrusion provided at the pivotal end 71B, as a result, when an individual tourniquet 30B is separated from the continuous tourniquets 3B, the spring-back of the tourniquets 3B towards the receiving cavity 13 due to the elasticity and restoring force of the tourniquets 3B is prevented. The first shaft 16B and the second shaft 15B are fixed to the box 1B, and the free end 72B is rotatable about the second shaft 15B.

The protrusions 5A and 5C of the box 1A are configured to automatically engage into the aperture 31A in the tourniquets 3A. During the extraction of the tourniquets, considering that the apertures 31A are formed at an interval of the predetermined length in the tourniquets 3A, the predetermined length is automatically identified when the protrusions 5A and 5C engage into the aperture 31A. Likewise, the protrusions 5B and 5D of the box 1A are configured to automatically engage into the aperture 31B in the tourniquets 3B. During the extraction of the tourniquets, considering that the apertures 31B are formed at an interval of the predetermined length in the tourniquets 3B, the predetermined length is automatically identified when the protrusions 5B and 5D engage into the aperture 31B.

Comparison Examples

The present invention is compared with CN patent No. 200920265929.1 by experiment results below.

1. Comparison by the Way of Shaping the Tourniquets

In the present invention, the tourniquets are wound around a shaft, so that less time is taken for winding the tourniquets of the same length, achieving higher efficiency, better consistence, and a uniform force for extracting the tourniquets.

In the prior art, the tourniquets are folded, but the folded portions have various shapes due to uneven thickness and hardness of different segments of the tourniquets, causing different resistance and hence different extracting forces in extracting the tourniquets and more time taken for folding the tourniquets.

Thus, compared with the prior art, the present invention is advantageous for: shorter time and higher efficiency for shaping the tourniquets, which is improved by 50% than the prior art, and the uniform force for extracting the tourniquets.

2. Comparison by Way of Movement of the Tourniquets in the Box.

In the present invention, the tourniquets undergo a circular motion by the cooperation between the fix shaft and the bearing.

This is beneficial in that: due to the cooperation between the fix shaft and the seat or bearing, the tourniquets are directly wound on the bearing or on the seat cooperating with the bearing, or the tourniquets are wound on the seat cooperating with the fix shaft, so that the rotation resistance is small, and a very small and uniform extraction force is required for the extraction of the tourniquets.

However, in the prior art, the tourniquets are subjected to S-shaped motion, which is defective for the large resistance and the uneven extraction force during the extraction.

Therefore, compared with the prior art, the present invention is advantageous for the small and even extraction force for the extraction of the tourniquets.

3. Comparison by Way of the Time and Precision for Identifying the Predetermined Length, i.e. the Length of the Individual Tourniquet.

In the present invention, the predetermined length of the individual tourniquet is automatically identified with high precision of 100% during the extraction.

In the prior art, it is required to insert the engaging protrusion into the aperture for tearing with eyes staring at the tourniquets, and the precision for identifying the predetermined length of the tourniquet is as low as 80%.

As for the time taken for the identifying, no additional time is required for the identifying because the identifying the predetermined length and the extracting the tourniquets is performed simultaneously. In the prior art, however, 2-5 seconds are required for identifying the individual tourniquet.

Therefore, compared with the prior art, the present invention is advantageous for the elimination of the additional time for identifying the predetermined length, whereas the additional time for identifying the predetermined length is long in the prior art.

4. Comparison by Way of the Extraction Forces for Extracting the Tourniquets at an Average Speed of 1 cm Per Second is as Follows:

in the present invention: 0.3~04. N; and in the prior art: 0.9~1.1 N.

Therefore, the extraction force required in the invention is merely about 30% of that in the prior art.

5. The Tension Force Applied for Tearing Off the Tourniquet

In the present invention, a test was conducted, where the protrusion extended through the aperture in the tourniquets, and the hook of a tension meter is attached to one end of the tourniquets which is away from the protrusion by a predetermined distance of 40 mm, to pull the tourniquets with a tension force at an angle of 45° from the horizontal direction until the tourniquet is torn off. The largest tension force is measured during the pulling. Ten such largest tension forces are obtained in ten such tests, and an average tension force of these largest tension forces is calculated as the tension force for tearing off the tourniquets, which is 4.5 N.

In the prior art, a test was conducted, where the tourniquets are fixed by the protrusion inserting into the tearing aperture, the hook of a tension meter is attached to one end of the tourniquets which is away from the protrusion by a predetermined distance of 40 mm, to pull the tourniquets with a tension force at an angle of 45° from the horizontal direction until the tourniquet is torn off. The largest tension force is measured during the pulling. Ten such largest tension forces are obtained in ten such tests, and an average tension force of these largest tension forces is calculated as the tension force for tearing off the tourniquets, which is 11 N.

Therefore, the tension force required for tearing off the tourniquet is merely about 40% of that in the prior art.

6. Comparison by Way of Success Rates of Tearing Off the Tourniquets

In the present invention, a test was conducted, where the aperture of the tourniquets is engaged with the protrusion, and one end of the tourniquets which is away from the protrusion by a distance of 70 mm is held by hand and pulled at an angle of 45°-55° from the horizontal direction to tear off the tourniquet. The test was conducted for 100 times and the success rate of tearing off the tourniquet is obtained as 99%.

In the prior art, a test was conducted, where the tourniquets are fixed by the protrusion inserting into the tearing aperture, and one end of the tourniquets which is away from the protrusion by a distance of 70 mm is held by hand and pulled at an angle of 45°-55° from the horizontal direction to tear off the tourniquet. The test was conducted for 100 times and the success rate of tearing off the tourniquet is obtained as 87%.

As can be seen, the success rate of tearing off the tourniquet according to the present invention is higher than that in the prior art by 12%.

The invention claimed is:

1. A structure for automatically identifying a predetermined length of a tourniquet, comprising a box and tourniquets, wherein the box has at least one receiving cavity in which the tourniquets are placed and an opening configured to be passed through by an end of the tourniquets, wherein apertures and tearing lines are respectively formed in the tourniquets at an interval of the predetermined length in a longitudinal direction of the tourniquets, with the apertures being respectively adjacent to the tearing lines, the box is provided with a protrusion configured to automatically extend through the apertures during the extraction of the tourniquets, and the apertures are configured to identify the predetermined length of the tourniquets and facilitate tearing off of the tourniquets during the tearing off of the tourniquets, wherein each of the tearing lines is ahead of the aperture adjacent thereto in an extraction direction of the tourniquets.

2. The structure of claim 1, wherein the apertures cooperate with the protrusions in a one-to-one relationship during the extraction of the tourniquets.

3. The structure of claim 1, wherein each of the apertures cooperate with two or more of the protrusions during the extraction of the tourniquets.

4. The structure of claim 1, further comprising a fixed shaft fixed to the box, wherein the fixed shaft is extended through a seat on which the tourniquets are wound.

5. The structure of claim 1, further comprising a fixed shaft fixed to the box, wherein the fixed shaft is extended through a bearing which is inserted into a seat, with the tourniquets being wound onto the seat.

6. The structure of claim 4, wherein a damping arrangement is provided between the seat and the box, and is configured to prevent unintentional rotation of the seat due to the inertia of the seat.

7. A method for automatically identifying a predetermined length of tourniquets and quickly tearing off the tourniquets, comprising: preparing a box having at least one receiving cavity; and placing the tourniquets within the receiving cavity, wherein the box is provided with an opening configured to be passed through by an end of the tourniquets, apertures and tearing lines are respectively formed at an interval of the predetermined length in a longitudinal direction in the tourniquets, with the apertures being respectively adjacent to the tearing lines, the box is provided with protrusions which are configured to automatically extend through and engage into the apertures during the extraction of the tourniquets out of the opening, so that the predetermined length of the tourniquets is automatically identified by the protrusions, and meanwhile the quick tearing off of the tourniquets at the aperture is facilitated by the protrusions.

8. The method of claim 7, wherein tearing lines overlapping with the apertures are formed in the tourniquets at an interval in the longitudinal direction, the protrusions automatically cooperate with and extend through the apertures during the extraction of the tourniquets out of the opening, so that the predetermined length of the tourniquets is automatically identified by the protrusions, and meanwhile the quick tearing off of the tourniquets at the aperture and the tearing lines is facilitated by the protrusions.

* * * * *